United States Patent [19]

Baker

[11] Patent Number: 5,026,903
[45] Date of Patent: Jun. 25, 1991

[54] PRODUCTION OF ETHYLIDENE DIACETATE FROM DIMETHYL ACETAL

[75] Inventor: Edgar C. Baker, Bridgewater, N.J.

[73] Assignee: Union Carbide Chemicals and Plastics Technology Corporation, Danbury, Conn.

[21] Appl. No.: 843,920

[22] Filed: Mar. 21, 1986

Related U.S. Application Data

[63] Continuation of Ser. No. 594,717, Mar. 29, 1984, abandoned.

[51] Int. Cl.$^5$ ...................... C07C 67/36; C07C 67/37; C07C 69/16
[52] U.S. Cl. ................................... 560/232; 560/240; 562/891
[58] Field of Search ........................ 560/232; 594/717

[56] References Cited

U.S. PATENT DOCUMENTS 2,255,950  6/1951  Wilson et al. ....................... 568/678
4,062,898  12/1977  Dubeck et al. ..................... 568/678

FOREIGN PATENT DOCUMENTS

28474A1  5/1981  European Pat. Off. ............ 560/261
28515A1  5/1981  European Pat. Off. ............ 560/232
35860A2  9/1981  European Pat. Off. ............ 560/232
1538782  1/1979  United Kingdom ................ 560/232

OTHER PUBLICATIONS

Migrdichian, Organic Synthesis, vol. 1, Reinhold Publishing Corp., N.Y. 1957, p. 326.

*Primary Examiner*—Vivian Garner
*Attorney, Agent, or Firm*—Reynold J. Finnegan; Henry H. Gibson

[57] ABSTRACT

A process for the production of ethylidene diacetate by the catalytic reaction of dimethyl acetal, methyl acetate and carbon monoxide in contact with a homogeneous catalyst system containing rhodium metal atom and lithium iodide.

5 Claims, No Drawings

PRODUCTION OF ETHYLIDENE DIACETATE FROM DIMETHYL ACETAL

This application is a continuation of prior U.S. application Ser. No. 594,717 filed Mar. 29, 1984 now abandoned.

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does not exist describing the production of ethylidene diacetate, to our knowledge it does not disclose or suggest our invention. Several pertinent references in this area are discussed below.

U.S. Pat. No. 2,555,950, issued on June 5, 1951 and assigned to E. I. duPont de Nemours & Co., discloses the process for reacting a 1,1-dimethoxy ether of an n-alkane with carbon monoxide and hydrogen in the presence of a cobalt hydrogenation catalyst as the sole catalytic agent. At column 3, line 41 et sequentia, the inventors describe the products obtained as being aldehydes or alcohols and specifically identify the products as 2-methoxy-1-propanal, 2-methoxy-1-propanol, 2-methoxy-1-butanal and 2-methoxy-1-butanol. There is no suggestion or disclosure on the use of a rhodium catalyst and lithium iodide or of the production of ethylidene diacetate.

U.S. Pat. No. 4,062,898, issued on Dec. 13, 1977 to M. Dubeck and G. G. Knapp and assigned to Ethyl Corporation, discloses the conversion of lower acetals to alcohols in the presence of a cobalt catalyst which may also contain iodine and ruthenium components. There is no suggestion or disclosure on the use of a rhodium catalyst, nor is there any indication in the patent, including the detailed examples, that ethylidene diacetate was produced or could be produced.

British Patent Specification 1,538,782, issued to N. Rizkalla and C. N. Winnick and published on Jan. 24, 1979 (Belgian equivalent, 839,321), and the references referred to therein, relate to the preparation of ethylidene diacetate by the reaction of methyl acetate and/or dimethyl ether with carbon monoxide and hydrogen in the presence of a halide and a Group VIII nobel metal catalyst under essentially anhydrous conditions. There is no disclosure or suggestion for the production of ethylidene diacetate from dimethyl acetal.

In European Patent Application No. 0028474A1, filed by T. Isshike et al and published on May 13, 1981, there is disclosed in the process for producing vinyl acetate a step in which acetaldehyde and dimethyl acetal are converted to ethylidene diacetate and methyl acetate using an acid catalyst. The suitable acid catalysts are disclosed on pages 14 to 16 of this publication. The reference contains no mention of the use of rhodium or its compounds in conjunction with lithium iodide nor of the carbonylation of dimethyl acetal with carbon monoxide to form ethylidene diacetate. A similar disclosure on the preparation of ethylidene diacetate from acetals is also shown in Japan Kokai 56-40642/81.

In European Patent Application No. 0028515A1, filed by T. Isshiki and published on May 13, 1981, there is disclosed the production of ethylidene diacetate by the reaction of carbon monoxide with dimethyl acetal, a Group VIII metal compound and an iodide or bromide. The publication makes no distinction as to the Group VIII metal and halide that can be employed with the examples showing the use of rhodium, palladium and nickel and methyl iodide as the sole reactants within the broad definition. The amount of methyl iodide used in the examples ranges from about 20% to about 35% by weight of the initial reactants charged to the reactor; the use of such high concentrations is not commercially acceptable due to its corrosivity and cost. The results reported in the examples of this reference indicate a best rate for production of ethylidene diacetate of about 0.25 mole/liter/hour.

In European Patent Application No. 0035860A2, filed by T. Isshiki and published on Sept. 16, 1981, ethylidene diacetate and/or acetaldehyde are produced by the hydrocarbonylation of methyl acetate or dimethyl ether with carbon monoxide and hydrogen in the presence of a palladium catalyst and a halide promoter. This is not our process. Further, the reference indicates on pages 3 and 4 that rhodium, platinum and ruthenium are poor catalysts.

It can be seen that the prior art contains many disclosures dealing with the catalytic production of ethylidene diacetate, including its production from dimethyl acetal. The art also discloses the production of other organic compounds from synthesis gas.

SUMMARY OF THE INVENTION

A catalyst system and process for the production of ethylidene diacetate by the reaction of mixtures of dimethyl acetal, methyl acetate and carbon monoxide has been found. The catalyst system charged to the reactor in our process contains rhodium atoms, lithium iodide and optionally an organic ligand. The use of lithium iodide in this system within the ranges defined results in unexpectedly improved efficiency, conversion rate or activity and selectivity.

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible. It must, also, not be excessively corrosive.

Stability of the catalyst relates to how long the catalyst remains functional before either breaking down or losing its catalytic effect.

Activity or conversion rate relates to the amounts of reactants the catalyst converts to product per unit of time, generally expressed in g. mole per liter per hour (g mole/l/hr).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective, improvement is always desirable.

The present invention is based on the unexpected and unpredictable discovery that the rhodium-lithium iodide-methyl acetate system is an improved catalytic system for the production of ethylidene diacetate from dimethyl acetal and carbon monoxide at unexpected improved efficiency, selectivity and conversion rate. It was also found that a ligand, $ER_3''$, can also be present as an optional component of the system. This unexpected improvement in efficiency, selectivity and conversion rate is achieved when the system's components are maintained within a defined range and when methyl acetate plus lithium iodide as the source of the halogen component, are present in the system. Optionally a solvent and/or diluent can also be present. The improved catalyst system of this invention can be portrayed as containing the components Rh—LiI—CH$_3$COOCH$_3$, wherein Rh is the rhodium containing compound; $ER_3''$ can optionally be present.

In the process of our invention dimethyl acetal is reacted with carbon monoxide in the presence of methyl acetate using a particular catalyst system containing rhodium atoms and lithium iodide. This system produces ethylidene diacetate at improved efficiency, conversion rate and selectivity, with a minimum of by-products. The reaction for the carbonylation of dimethyl acetal to ethylidene diacetate is:

$$CH_3CH(OCH_3)_2 + 2CO \rightarrow CH_3CH(OOCCH_3)_2$$

The rhodium component of the catalyst system can be supplied from any number of sources, many of these are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_2$
$RhCl_3\ 3H_2O$
$RhBr_3\ 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$RhCl[(C_6H_5)_3P]_2(CH_3I)_2$
$Rh(SnCl_3)[(C_6H_5)_3P]_2$
$RhCl(CO)[(C_6H_5)_3As]_2$
$RhI(CO)[(C_6H_5)_3Sb]_2$
$[(n-C_4H_9)_4N][Rh(CO)_2X_2]$ where $X=Cl-, Br-, I-$
$[(n-C_4H_9)_4As]_2[Rh(CO)_2X_4]$ where $X=Br-, I-$
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI[(C_6H_5)_3P]_3$
$RhCl[(C_6H_5)_3P]_2$
$RhCl[(C_6H_5)_3P]_3H_2$
$[(C_6H_5)_3P]_3Rh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The rhodium metal atom concentration can vary over a wide range. Enough metal atom must be present to achieve reasonable reaction rates; however, an excess may on occasion result in undesired by-products formation. The mole ratio of rhodium atom to dimethyl acetal can vary from 1:25 to 1:20,000, the preferred range is from about 1:4 to 1:1000, with the most preferred range being from about 1:100 to 1:500. The amount used is not a critical feature in this invention and higher rhodium concentrations are acceptable but are influenced by economic considerations.

The second component of the catalyst system is lithium iodide. It can be charged directly, or it can be formed in situ by any combination of lithium compound and iodine component that will result in the formation of lithium iodide during the reaction but preferably prior to the start of the reaction. Lithium bromide can also be used but the iodide is preferred. The presence of lithium iodide or lithium bromide and methyl acetate are a critical feature of this invention. Direct charge of lithium iodide is the preferred form. However, any convenient combination of compounds for in situ formation of lithium iodide can be used as indicated above. This includes the use of lithium carboxylates, carbonates and the like with a halogen compound such as iodine or an alkyl halide. A suitable combination for in situ formation is lithium carboxylate and an alkyl halide.

Sufficient lithium iodide must be present to exert a promoting effect on the reaction and to result in high efficiency, conversion rate and selectivity to the corresponding organic acid. The mole ratio of Rh:LiI can vary over a wide range. A Rh:LiI mole ratio of from 1:1 to 1:1000 can be employed, the preferred range is from about 1:2 to 1:200 and most preferably it is from about 1:8 to 1:150.

As indicated, an organic ligand of the general formula $ER_3''$ can optionally be present in the reaction system. The use of such ligands is known, as are their identities, to those skilled in this art. In this formula E represents a Group VA element, e.g., N, P, As, Sb and Bi, and R'' represents an organic moiety. The ligand can serve as a catalyst stabilizer and/or to further enhance efficiency, conversion rate and selectivity, especially when the reaction is carried out at higher temperatures, for example at about 200° C. or above. The ligand may also serve to inhibit equipment corrosion in some instances. However, the use of a ligand is not mandatory and the reaction can be carried out without it.

A large number of organic ligands is known and any of these can be used provided they do not have an adverse effect on the reaction. Among those of particular utility are the tertiary amines and the tri- and pentavalent phosphorus compounds. Though those skilled in the art know these compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutyl stearylphosphine, tribenzylphosphine, dipropyl phenylphosphine, ethyl dipropylphosphine, tricyclohexylphosphine, cyclohexyl dibutylphosphine, propyl diphenylphosphine, dipropyl phenylphosphine, phenyl diethylphosphine, tridecylphosphine, trioctadecylphosphine, tribenzylphosphine, methyl diethylphosphine, ethyl diphenylphosphine, tolyl diethylphosphine, cyclohexyl diethylphosphine, diethyl cyclohexylphosphine, bis-(diphenylphosphino)-ethane, bis-(diethylphosphine)-propane, bis-(diphenylphosphino)-butane, bis-(diethylphosphine)-octane, trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chlorophenyl)-amine, dibutyl phenylamine, dipentyl cyclopentylamine, ethyl diphenylamine, trinaphthylamine, tri-p-tolylamine, tri-benzylamine, tri(3-methylcyclohexyl)amine, and the arsines, stibines and bismuthines corresponding to the above-identified phosphines and amines. These and many others are known in the art. They can be used singly or, if one desires, mixtures containing two or more ligands can be used. One can also employ a phosphine oxide or phosphite corresponding to the above phosphines as the ligand; these are also well known.

The concentration of ligand charged can vary from a molar ratio of ligand to rhodium of from about 50:1 to 1:50, preferably from 10:1 to 1:10, most preferably about 3:1 to 1:1.

The present invention does not require the use of acidic halogen promoters, it employs the alkali metal halide lithium iodide. Nor does it require the presence of water or use of large quantities of methyl iodide to give high selectivity.

Also essential to this invention is the presence of methyl acetate. The methyl acetate is believed to exert a dual role, as reactant and as solvent. Though not intended to be bound by any theory, it is believed that in the reaction methyl acetate is carbonylated to acetic anhydride. The anhydride reacts with the dimethyl acetal to produce ethylidene diacetate and methyl acetate is regenerated. In the ideal stoichiometry there is no net consumption of methyl acetate; however, in practice some which is converted to acetic anhydride is lost from the reactor during the process. This theoretical explanation appears to be supported by some evidence. When dimethyl acetal is directly reacted with carbon monoxide, in the complete absence of methyl acetate, using a Group VIII metal - iodide catalyst system, the major products are acetaldehyde and methyl acetate along with some polymeric material. Ethylidene diacetate is not produced. Thus, methyl acetate, though not consumed, is a critical component in our process. The molar ratio of dimethyl acetate to methyl acetate should not exceed about 1:1. Too high a ratio of acetal to acetate leads to unwanted side reactions. Too low a ratio may result in an unacceptable decrease in the rate of product formation. Preferred ratio is from 1:1 to 1:5.

The reaction is carried out at a temperature of from about 100° C. to 250° C., preferably from 120° C. to 220° C. and most preferably from 150° C. to 180° C. When the reaction is carried out at temperatures above 200° C. in the presence of an $ER_3''$ ligand, the preferred ligands are the phosphines, especially triphenyl phosphine.

The pressure of the reaction can be from about 100 psig to 10,000 psig, preferably from 200 psig to 5,000 psig, most preferably from 500 psig to 2,000 psig.

The reaction time varies depending upon the reaction parameters, reactor size and charge, and the individual components employed as the specific process conditions. The reaction can be a batch or continuous reaction.

The experiments and examples detailed below were carried out in a Hasteloy ® steel autoclave reactor having a volume of 100 ml, which was equipped with temperature and pressure sensing means, heating and cooling means, agitator and inlet and outlet means for introducing and removing components from the reactor. The autoclaves used in synthesis gas reactions are well known in the art and can be used in this process.

Prior to charging the reactants the autoclave was washed with tetrahydrofuran, drained and dried with nitrogen. The liquid components were charged to the cleaned autoclave first and then the solid components were added and stirred. The autoclave was closed, purged with carbon monoxide and then pressurized to about 600 psig with carbon monoxide. The autoclave contents were heated to the selected temperature, with agitation (usually 750 rpm), in about 15 to 30 minutes. After the desired temperature was reached, carbon monoxide was introduced and the reactor was brought to the desired pressure. The reaction was allowed to proceed until the pressure had fallen by 500 psig, then the reactor was represented. After the reaction had been completed, the reactor contents were cooled to room temperature, the reactor was vented, flushed with nitrogen and the liquid contents drained, weighed and analyzed by gas chromatography. Precautions were taken to remove and destroy metal carbonyl that may have formed.

The following examples serve to further illustrate this invention.

EXAMPLE 1

The autoclave was charged with 17.5 g of methyl acetate (0.23 mol), 21 g of dimethyl acetal (0.23 mol), 1.3 mmoles of rhodium trichloride hydrate, 72 mmoles of lithium iodide, and 2.6 mmoles of triphenylphosphine. The reactor was heated to 180° C. and pressurized to 1,500 psig. Carbon monoxide was added, as indicated supra, as needed while the reaction proceeded for 40 minutes. The products were recovered as described above. Analysis of the products showed that 8 g of ethylidene diacetate, 6.1 g of methyl acetate and 14 g of acetic anhydride were produced during this short period of time. The rate to ethylidene diacetate was 1.5 moles per liter per hour.

EXAMPLE 2

The autoclave was charged with 17.5 g of methyl acetate (0.23 mol), 21 g of dimethyl acetal (0.23 mol), 1.5 mmoles of rhodium trichloride hydrate, 45 mmoles of lithium iodide and 6 mmoles of triphenylphosphine. The reactor was heated to 180° C. and pressurized to 1,500 psig. Carbon monoxide was added, as indicated supra, as needed while the reaction proceeded for 30 minutes. The products were recovered as described above. Analysis of the products showed that 5.8 g of ethylidene diacetate, 16.5 g of methyl acetate and 7 g of acetic anhydride were produced during this period of time. The rate to ethylidene diacetate was 1.6 moles per liter per hour.

These examples show the effectiveness of lithium iodide per se as the iodide promoter. The dimethyl acetal is charged at a 1:1 molar ratio with methyl acetate, which is not possible with methyl iodide as the promoter, and the rates to ethylidene diacetate are at least six times greater than those observed using methyl iodide in Comparative Experiments A and B.

Two comparative experiments were performed using methyl iodide as the source of the iodide promoter.

COMPARATIVE EXPERIMENT A

This experiment corresponds to the first example in EP28,515 in catalyst composition and total dimethyl acetal charged. The autoclave was charged with 30 g of methyl acetate, 4.5 g dimethyl acetal, 0.67 mmole of rhodium trichloride hydrate, 100 mmoles of methyl iodide and 2.6 mmoles of triphenylphosphine. The reactor was purged with carbon monoxide, heated to 180° C. and pressurized to 1,500 psig with carbon monoxide for a 2 hour period. The reactor was cooled and the products recovered includes 18 g of methyl acetate, 1.35 g of acetic anhydride and 3.3 g of ethylidene diacetate. The rate to ethylidene diacetate was 0.25 moles per liter per hour. The rate to ethylidene diacetate was lower than in Example 1.

COMPARATIVE EXPERIMENT B

The same autoclave was charged with 30 g of methyl acetate, 9 g of dimethyl acetal, 0.67 mmoles of rhodium trichloride hydrate, 100 mmoles of methyl iodide and 2.6 mmoles of triphenylphoshine. After purging with carbon monoxide it was heated to 180° C. and pressurized to 1,500 psig with carbon monoxide for a 3 hour period. The products recovered included 21.5 g of methyl acetate, 6 g of acetic anhydride and 4.2 g of etehylidene diacetate. The rate to ethylidene diacetate was 0.2 mole per liter per hour. The results showed that rate and selectivity decrease when the dimethyl acetal concentration are increased using this catalyst system.

Additional experiments showed that further increases in dimethyl acetal concentration resulted in even less ethylidene diacetate production and the precipitation of polymeric solids. Still further experiments, using the 1:1 molar ratio of dimethyl acetal to methyl acetate used in Examples 1 and 2 and the catalyst system of Comparative Example B were not fruitful; the experiments were considered unsuccessful because the amount of solids formed precluded meaningful analysis. Rate and selectivity to ethylidene diacetate were zero.

COMPARATIVE EXPERIMENT C

Thus was run in the same manner as Comparative Experiment B except that it used 50 mmoles of methyl iodide and 50 mmoles of lithium iodide and the reaction proceeded for 2.5 hours. There was recovered 8.2 g of methyl acetate, 23.3 g of acetic anhydride and 6.1 g of ethylidene diacetate. The rate to ethylidene diacetate was 0.35 mole per liter per hour. This comparative experiment shows that a mixture of methyl iodide and lithium iodide is not as good as a pure lithium iodide system and exhibits only 25% of the productivity of the pure lithium iodide system.

Thus, it is the specific use of the pure lithium iodide system that surprisingly produces, unexpectedly and unpredictably, the beneficial results.

EXAMPLES 3 AND 4

In these examples the autoclave was charged with 17.5 g of methyl acetate (0.23 mol) and 21 g of dimethyl acetal (0.23 mol). The catalyst system consisted of 1.5 mmoles of rhodium trichloride hydrate, 45 mmoles of lithium iodide and another promoter, as tabulated below. The reaction was carried out as described in Example 1 under the conditions shown in the tabulation; also included are the results achieved

| Example | 3 | 4 |
|---|---|---|
| Promoter, mmoles | | |
| Triphenylphosphine | 6 | — |
| Triphenylamine | — | 3.2 |
| Temperature, °C. | 150 | 180 |
| Time, hours | 2.5 | 0.5 |
| Products, g | | |
| Methyl acetate | 15.4 | 10.4 |
| Acetic anhydride | 9.2 | 11.9 |
| Ethylidene diacetate | 10.6 | 7.3 |
| Rate to ethylidene diacetate, mole per liter per hour | 0.6 | 2.0 |

These examples further substantiate the effectiveness of lithium iodide and the necessity of methyl acetate as the reactive solvent.

I claim:

1. A process for the production of ethylidene diacetate by the reaction of mixtures of dimethyl acetal, methyl acetate and carbon monoxide in contact with a homogeneous catalyst system consisting essentially of a rhodium component and a lithium iodide component, and optionally a ligand of the formula $ER_3^{11}$ wherein E is a Group VA element selected from the group consisting of nitrogen, phosphorus, arsenic, antimony and bismuth and where $R^{11}$ is an organic moiety, at a temperature of from about 100° C. to 250° C. and a pressure of about 100 psig to 10,000 psig, and wherein the rhodium component is provided for by rhodium or a compound of rhodium and wherein the lithium iodide component is provided for by a direct charge of lithium iodide.

2. A process as claimed in claim 1 wherein the mole ratio of Rh:LiI is from 1:1 to 1:1,000.

3. A process as claimed in claim 1 wherein the mole ratio of Rh:LiI is from 1:8 to 1:150.

4. A process as claimed in claim 1 wherein said ligand is a phosphine.

5. A process as claimed in claim 1 wherein said ligand is an amine.

* * * * *